(12) United States Patent
Jackson

(10) Patent No.: US 6,483,587 B1
(45) Date of Patent: Nov. 19, 2002

(54) GAP/EDGE BEAD DETECTION SYSTEM

(76) Inventor: John Charles Jackson, 422 Revere St., Clifton Forge, VA (US) 24422

(*) Notice: Subject to any disclaimer, the term of this patent is extended or adjusted under 35 U.S.C. 154(b) by 0 days.

(21) Appl. No.: 09/343,875

(22) Filed: Jun. 30, 1999

(51) Int. Cl.⁷ .................. G01N 21/84; G01B 11/06
(52) U.S. Cl. .................................................. 356/430
(58) Field of Search ..................... 356/430, 431, 356/630–632, 237.1–237.6, 239.1–241.1

(56) References Cited

U.S. PATENT DOCUMENTS

| | | |
|---|---|---|
| 2,644,496 A | 7/1953 | Schubert |
| 2,665,793 A | 1/1954 | Hardy |
| 2,797,610 A | 7/1957 | Coakley |
| 3,526,204 A | 9/1970 | Schnedler et al. |
| 3,564,530 A | 2/1971 | Kroeck et al. |
| 3,577,955 A | 5/1971 | Palmer |
| 3,723,991 A | 3/1973 | Schwartz |
| 3,771,737 A | 11/1973 | Swann |
| 4,357,899 A | 11/1982 | Jones et al. |
| 4,487,790 A | 12/1984 | Bergeron et al. |
| 5,067,436 A | 11/1991 | Matsushima et al. |
| 5,136,974 A | 8/1992 | Lisec |
| 5,318,629 A | 6/1994 | Raque et al. |
| 5,534,067 A | 7/1996 | Fulker et al. |
| 5,641,357 A | 6/1997 | Yamada et al. |
| 5,672,376 A | 9/1997 | Wallace |
| 5,745,244 A * | 4/1998 | Svanqvist et al. .......... 356/431 |
| 5,762,252 A | 6/1998 | Reitano |
| 5,786,036 A | 7/1998 | Pannenbecker et al. |
| 5,876,502 A | 3/1999 | Sugimura et al. |

* cited by examiner

Primary Examiner—Frank G. Font
Assistant Examiner—Amanda Merlino
(74) Attorney, Agent, or Firm—D. L. Bowman; R. L. Schmalz

(57) ABSTRACT

This invention relates to gap/edge bead detection systems. Such structures of this type, generally, employ the use of fiber optic sensor assemblies positioned at the edges of the web and/or between gaps in the sheets in order to detect the absence of material.

16 Claims, 3 Drawing Sheets

GAP/EDGE BEAD DETECTION SYSTEM

BACKGROUND OF THE INVENTION

1. Field of the Invention

This invention relates to gap/edge bead detection systems. Such structures of this type, generally, employ the use of fiber optic sensor assemblies positioned at the edges of the web and/or between gaps in the sheets in order to detect the absence of material.

2. Description of the Related Art

Extrusion coating is a process where a moving paper web is coated with a molten polymer layer. The polymer layer usually extends beyond the paper web, thereby creating a "polymer edge bead". It is important that the polymer bead be present to insure that the entire web has been coated. Some polymers are difficult to control at the extrusion extremities of the paper web and/or sheet. These polymers are subject to occasional and unpredictable "wicking in", i.e., the edge of the polymer layer moves inside the edge of the paper web. This "wicking in" can be as much as several inches and may continue for just a few seconds or sometimes until corrective action is taken by the operator. Also, the absence of polymer along the entire web is a serious quality defect that can be catastrophic for the customer's product.

It is known to employ detection systems that use cameras to monitor the web. However, these are very expensive and highly sensitive. Also, these systems often require the web to be shielded from the surroundings.

It is also known to employ photo sensors to inspect a material edge and control process conditions within tolerances required by production. Exemplary of such prior art is U.S. Pat. No. 4,357,899 ('899) to Jones et al., entitled "Coating Apparatus". The major focus of the '899 reference is in controlling a liquid coating process through reservoir design tanks. However, the inspection system of the '899 reference cannot be employed on both a sheeting machine where it senses the gap between sheets and on an extrusion coating line where it senses the presence or absence of a polymer coating at the edge of a continuous sheet.

Therefore, it is apparent from the above that there exists a need in the art for a highly accurate and economically reliable gap and edge bead detection for a variety of extruded coatings. The detection system should function without regard to material characteristics such as color, temperature, thickness or chemical make-up. The chemical system should also be unaffected by the physical surroundings. It is a purpose of this invention to fulfill this and other needs in the art in a manner more apparent to the skilled artisan once given the following disclosure.

SUMMARY OF THE INVENTION

Generally speaking, this invention fulfills. these needs by providing an edge bead detection system, comprising a frame means, a length of material having a coating located over a portion of the length of material, a slidable mounting means operatively connected to the frame means, an edge bead detection means operatively connected to the mounting means and located a predetermined distance away from the length of material, and a retaining means operatively connected to the mounting means.

In another further preferred embodiment, the detection system is capable of sensing the gap between sheets and the presence or absence of polymer coating along the edge of a continuous sheet without regard to material characteristics such a color, temperature, thickness or chemical make-up. Also, the detection system is unaffected by the physical surroundings.

The preferred system, according to this invention, offers the following advantages: lightness in weight; ease of assembly and repair; good stability; good durability; excellent economy; excellent detection characteristics; excellent sensing characteristics; mobility of location and relocation; physical protection; and ability to realign. In fact, in many of the preferred embodiments, these factors of detection, sensing, mobility of location and relocation, physical protection, and ability to realign are optimized to the extent that is considerably higher than heretofore achieved in prior, known detection systems.

The above and other features of the present invention, which will become more apparent as the description proceeds, are best understood by considering the following detailed description in conjunction with the accompanying drawings, wherein like characters represent like parts throughout the several views and in which:

A BRIEF DESCRIPTION OF THE DRAWINGS

DETAILED DESCRIPTION OF THE INVENTION

Figure 1:
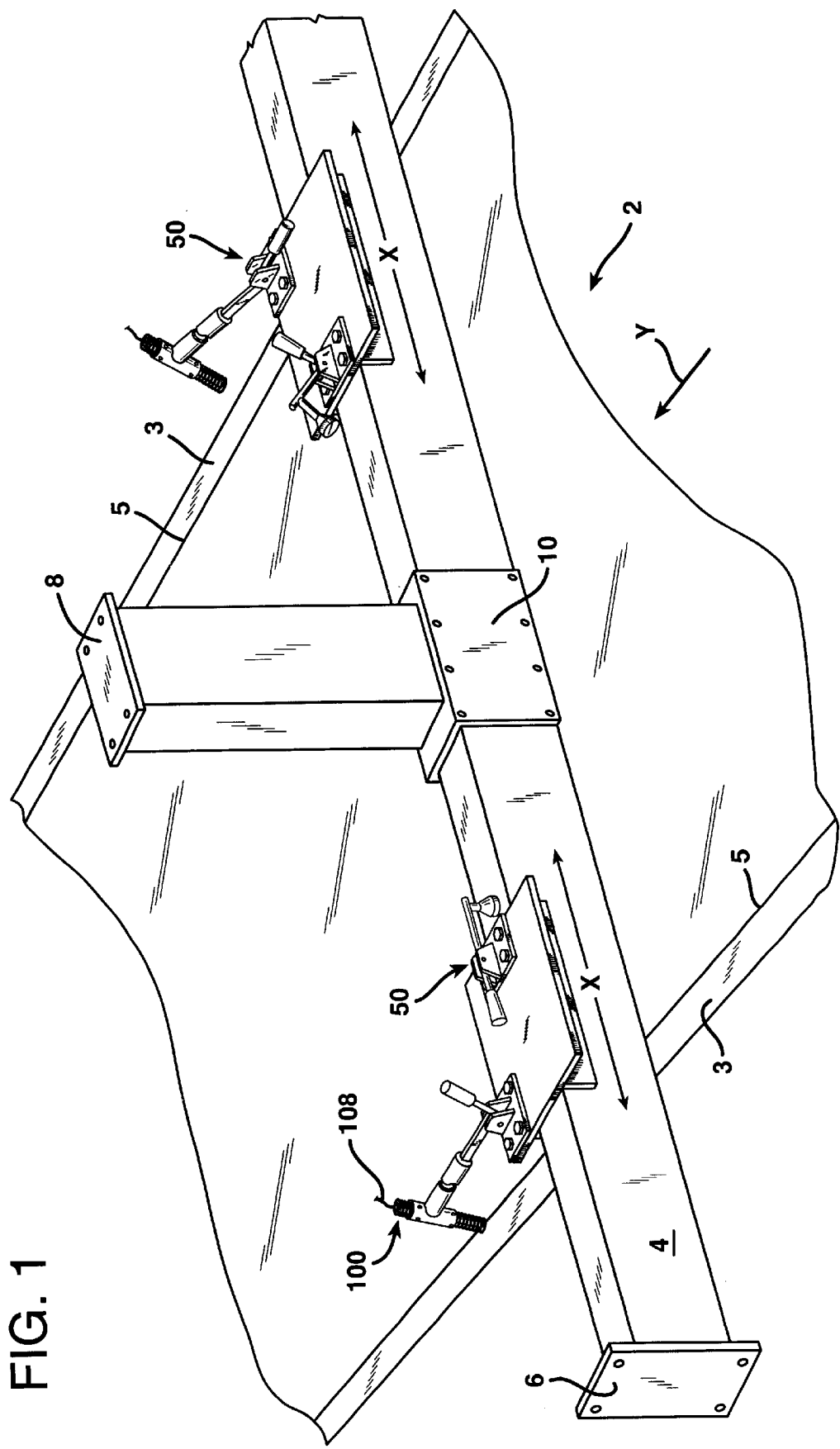
FIG. 1 is an isometric view of a gap/edge bead detection system, according to the present invention.

With reference first to FIG. 1, there is illustrated an advantageous environment for use of the concepts of this invention. In particular, gap/edge bead detection system 2 is illustrated. System 2 includes, in part, length of material 3, frame 4, conventionally extruded coating 5, bracket 6, mid support 8, removable cover 10, raising/lowering latch mechanism 50, and gap/edge bead detection mechanism 100. Preferably, frame 4, bracket 6, mid support 8 and cover 10 are constructed of any suitable, durable material. Frame 4 is rigidly attached to bracket 6 and mid support 8 by conventional techniques. Length of material 3 can either be a length of a conventional roll of material or a length of a conventional sheet of material. Cover 10 can be conventionally removed in order to allow ease of frame alignment during installation.

Figure 2:
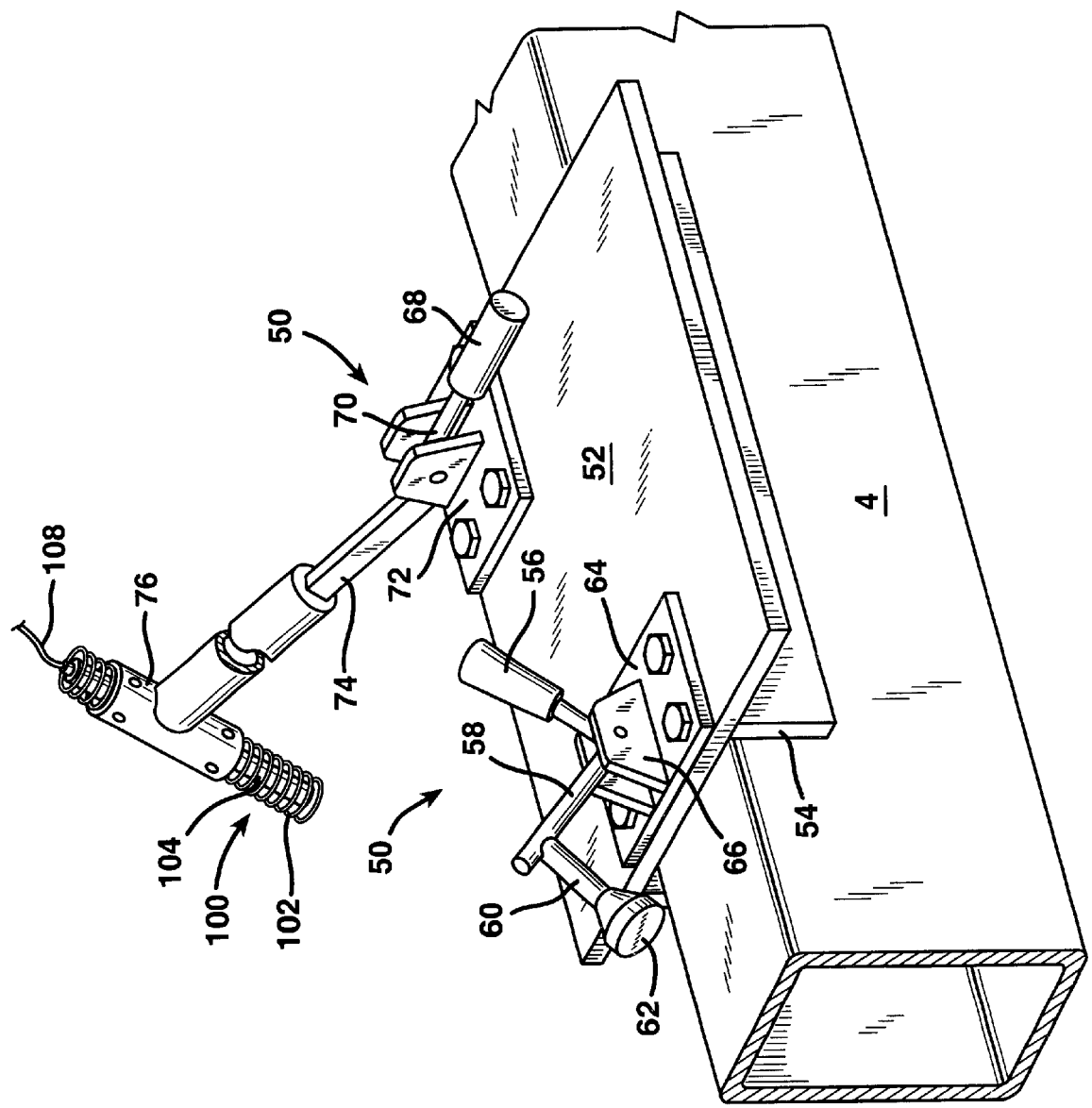
FIG. 2 is an isometric view of the slidable mount which is attached to the gap/edge bead detection means, according to the present invention.

As shown in FIG. 2, latch mechanism 50 is illustrated. Mechanism 50 includes, in part, base 52, guide 54, arm 56, arm 58, extension 60, stop 62, pivot base 64, pivot 66, arm 68, pivot 70, pivot base 72, arm 74, gap/edge bead detector holder 76 and gap/edge bead detector mechanism 100.

Preferably, base 52, guide 54, arm 56, arm 58, extension 60, pivot base 64, pivot 66, arm 68, pivot 70, pivot base 72, arm 74, and gap/edge bead detector holder 76 are constructed of any suitable, durable material. Stop 62, preferably, is constructed of any suitable material which, when interacting with frame 4, prevents mechanism 50 from sliding along the direction of arrow X (FIG. 1).

The construction of base 52 and guide 54 should be such that it fits over frame 4 and easily slides along the direction of arrow X (FIG. 1). Pivot base 64 is rigidly attached to base 52 by conventional techniques. Arms 56 and 58 are conventionally latched to base 64 by latch 66 such that when arm 56 is pulled up away from frame 4, arm 58 pivots up and raises extension 60 and stop 62 away from frame 4. In this manner, base 52 is able to slide along frame 4 in the direction of arrow X (FIG. 1).

Arm 68 is pivotedly attached to arm 74 at pivot 70. Pivot 70 is conventionally attached to pivot base 72. Pivot base 72 is conventionally attached to base 52. In this manner, when arm 68 is pushed down towards frame 4, this causes gap/edge bead detection mechanism 100 to raise above length of material 3 which is traveling in the direction of arrow Y (FIG. 1).

Figure 3:
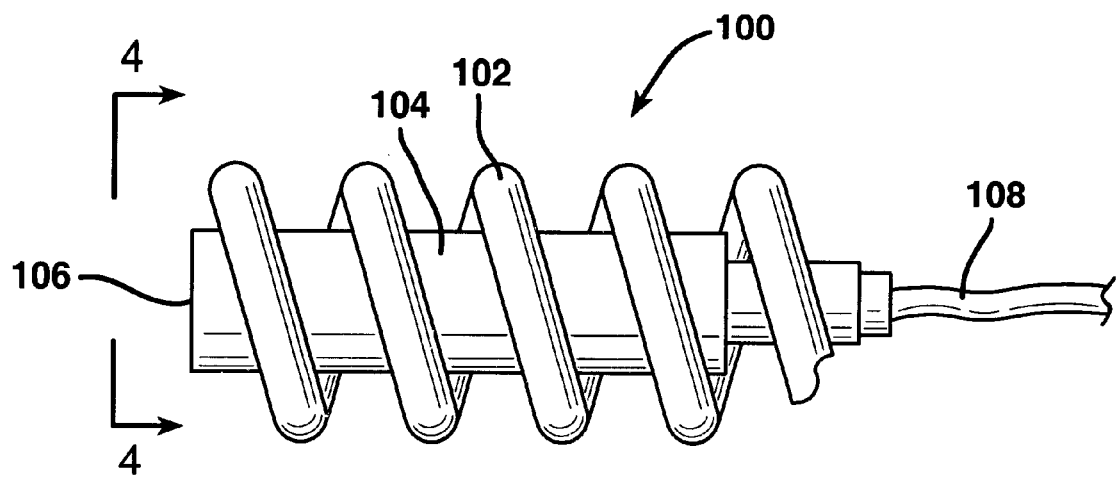
FIG. 3 is a side, plain view of the gap/edge bead detection means, according to the present invention.

FIG. 3 more clearly illustrates gap/edge bead detection mechanism 100. Mechanism 100 includes, in part, conventional coiled spring 102, conventional bushing 104, conventional fiber optic sensor head 106, and conventional sensor cable head 108. Sensor cable head 108 is conventionally attached to an electronic control unit (not shown) which controls the coating of length of material 3. It is to be understood that the control unit can be connected to a conventional alarm system (not shown) to alert the operator if mechanism 100 does not sense any coating.

Figure 4:
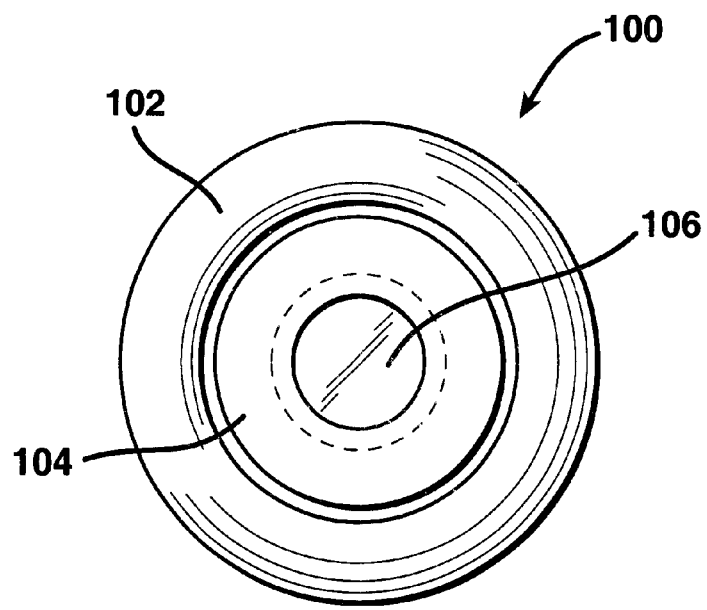
FIG. 4 is an end view, taken along line 4—4 of FIG. 3, of the gap/edge bead detection means.

As more clearly shown in FIG. 4, bushing 104 is constructed of an outside diameter which is slightly larger than the inside diameter of coiled spring 102. This allows bushing 104 to be pressure fitted into the end of coiled spring 102. The center of bushing 104 is conventionally drilled and tapped to allow sensor head 106 to be screwed into bushing 104. This provides infinite depth adjustment and a secure mounting for sensor head 106.

The gap/edge bead detection system 2 is manually operated and provides for two detection systems, one on each edge of the paper web. The horizontal location of detection mechanism 100 is infinitely variable. The operator simply slides the detection mechanism 100 to match the edge of length 3 being processed. The vertical gap between detection mechanism 100 and edge bead 5 is fixed and maintained by latch mechanism 50. Latch mechanism 50 is in working position when lowered. The vertical position is also shown as a manual operation. These two positioning functions can be automated using commercially available position technology and engineering.

Sensor mechanism 100 consists of a fiber optic bundle and spring assembly. The purpose of spring 102 is to allow for process upsets, such as web breaks, to occur without destroying detection mechanism 100. Detection mechanism 100 can bend out of the way if contacted by a portion of length of material 3 during an upset. For example, the tail of the previous roll retained with in the web on a splice can flap into the air and strike detection mechanism 100. Spring 102 serves as a shield and is self-aligning in that it also brings sensor head 106 back into the proper position to resume gap/edge bead detection.

It is to be understood that detection mechanism 100 can also employed to detect gaps between lengths of material 3. In particular, detection mechanism 100 can be located in one position so as to detect an edge of coating 5 and also to detect when there is a gap between lengths of material 3.

The fiber optic detection mechanism 100 was chosen for several reasons. Sensor head 106 reacts very quickly and is sensitive over a wide range of colors. Sensor head 106 is capable of detecting an object of only 0.001" thickness even when laying on a solid surface. Sensor head 106 is autoreflective, i.e., it is self-contained, requiring only the present or absence of an object. An opposing light source or reflector of a through beam signal is not required. Finally, detection mechanism 100 is relatively inexpensive and highly reliable for millions of operations.

Finally, detection system 2 can be interfaced with any appropriate warning device (e.g., buzzer, lights) which is commercially available. A conventional web and/or sheet marketing system could also be interfaced with the detection system 2 to flag defective product. Also, detection system 2 can be conventionally connected to a conventional coater (not shown). In this manner, if a defect is detected by system 2, an alarm may sound, the sheet may be marked and/or the coater may be activated to provide coating.

Once given the above disclosure, many other features, modifications or improvements will become apparent to the skilled artisan. Such features, modifications or improvements are, therefore, considered to be a part of this invention, the scope of which is to be determined by the following claims.

What is claimed is:

1. An edge bead detection system for detecting a bead along a length of material comprising:
   a length of material having a coating located above a portion of said length of material;
   a frame means located over above a portion of said length of material;
   a moveable mounting means operatively secured to said frame means;
   an edge bead detection means comprising a self-aligning sensor head assembly with a coiled spring means a bushing means located substantially along one end of said coiled spring means; and a adjustable sensor head located substantially within said bushing means, wherein said edge bead detection means is operatively secured to said mounting means and located a predetermined distance away from said length of material; and
   a retaining means operatively secured to said mounting means.

2. The edge bead detection system as in claim 1, wherein said mounting means comprises:
   a first base plate means operatively secured to said frame means; and
   a guide means secured to said base plate means and operatively secured to said frame means.

3. The edge bead detection system as in claim 1, further comprising a first latch means secured to said mounting means.

4. The edge bead detection system as in claim 3, wherein said self-aligning sensor head assembly is operatively secured to said first latch means.

5. The edge bead detection system as in claim 1, wherein said adjustable sensor head assembly comprises a fiber optic sensor head.

6. The edge bead detection system as in claim 3, wherein said first latch means comprises:
   a second base means secured to said base plate means;
   a first arm means;
   a first pivot means operatively secured to said second base means; and
   a second arm means pivotedly secured to said first arm means by said first pivot means and operatively secured to the other end of said coiled spring means.

7. The edge bead detection system as in claim 6, wherein said retaining means comprises:
   a third base means secured to said first base means;
   a third arm means;

a second pivot means operatively secured to said third base means; and a fourth arm means pivotedly secured to said third arm means by said second pivot means and secured to a stopping means.

8. The edge bead detection system, as in claim 7, wherein said stopping means is further comprised of:

an extension means rigidly attached at one end to said fourth arm means; and a stopper operatively attached to the other end of said extension means.

9. A gap detection system for detecting a gap between lengths of material comprising:

a plurality of lengths of material having a gap between each of said plurality of lengths of material;

a frame means located above said plurality of lengths of material;

a moveable mounting means operatively connected to said frame means;

a gap detection means comprising a self aligning sensor head assembly with a coiled spring means, a bushing means located substantially along one end of said coiled spring means, and an adjustable sensor head located substantially within said bushing means wherein said gap detection means is operatively secured to said mounting means and located a predetermined distance away from said plurality of lengths of material; and a retaining means operatively secured to said mounting means.

10. The gap detection system as in claim 9, wherein said mounting means comprises:

a first base plate means operatively secured to said frame means; and a guide means secured to said first base plate means and operatively secured to said frame means.

11. The gap detection system as in claim 9, wherein said gap detection means further comprises a first latch means secured to said mounting means.

12. The gap detection system as in claim 11, wherein said self-aligning sensor head assembly is operatively secured to said first latch means.

13. The gap detection system as in claim 9, wherein said adjustable sensor head comprises a fiber optic sensor head.

14. The gap detection system as in claim 11, wherein said first latch means comprises:

a second base means secured to said base plate means;

a first arm means;

a first pivot means operatively secured to said second base means; and a second arm means pivotedly secured to said first arm means by said first pivot means and operatively secured to the other end of said coiled spring means.

15. The gap detection system as in claim 14, wherein said retaining means comprises:

a third base means secured to said first base means;

a third arm means;

a second pivot means operatively secured to said third base means; and a fourth arm means pivotedly secured to said third arm means by said second pivot means and secured to a stopping means.

16. The gap detection, as in claim 15, wherein said stopping means is further comprised of:

an extension means rigidly attached at one end to said fourth arm means; and a stopper operatively attached to the other end of said extension means.

* * * * *